US012016579B2

United States Patent
Anderson et al.

(10) Patent No.: US 12,016,579 B2
(45) Date of Patent: Jun. 25, 2024

(54) STEERABLE CROSSING CATHETER

(71) Applicant: BOSTON SCIENTIFIC SCIMED, INC., Maple Grove, MN (US)

(72) Inventors: Jason T. Anderson, Deephaven, MN (US); Patrick A. Haverkost, Corcoran, MN (US); John Harris Mundahl, Golden Valley, MN (US); John James Ling Laroy, Minneapolis, MN (US); Raed N. Rizq, Maple Grove, MN (US); Joel M. Wasdyke, Eden Prairie, MN (US); Rowan Olund Hettel, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 695 days.

(21) Appl. No.: 17/165,182

(22) Filed: Feb. 2, 2021

(65) Prior Publication Data
US 2021/0236776 A1     Aug. 5, 2021

Related U.S. Application Data

(60) Provisional application No. 62/969,252, filed on Feb. 3, 2020.

(51) Int. Cl.
*A61B 17/22*     (2006.01)
*A61M 25/00*     (2006.01)
(Continued)

(52) U.S. Cl.
CPC ......... *A61B 17/22* (2013.01); *A61M 25/0068* (2013.01); *A61M 25/0138* (2013.01);
(Continued)

(58) Field of Classification Search
CPC .. A61B 2017/22094; A61B 2017/3413; A61B 2017/00309; A61B 2017/00106; A61B 2017/00022; A61B 17/22
See application file for complete search history.

(56) References Cited

U.S. PATENT DOCUMENTS 5,263,959 A * 11/1993 Fischell ............ A61B 17/3207
606/167
5,941,869 A     8/1999 Patterson et al.
(Continued)

FOREIGN PATENT DOCUMENTS

WO     2016160712 A1     10/2016
WO     2019204797 A1     10/2019

OTHER PUBLICATIONS

International Search Report and Written Opinion dated May 31, 2021 for International Application No. PCT/US2021/016171.

*Primary Examiner* — Katherine H Schwiker
(74) *Attorney, Agent, or Firm* — Seager, Tufte & Wickhem LLP

(57) ABSTRACT

Medical devices as well as methods for making and using medical devices are disclosed. An example medical device may include a steerable crossing catheter system. The steerable crossing catheter system may include an elongate catheter shaft having a proximal end region, a steerable distal end region, and a lumen extending therethrough. A core may be disposed within the lumen. The core may have a distal end. A penetrating member may be coupled to the distal end. A sensing assembly may be disposed adjacent to the distal end. The sensing assembly may be configured to estimate the location of the core within a body lumen.

20 Claims, 9 Drawing Sheets

(51) Int. Cl.
*A61M 25/01* (2006.01)
*A61B 17/00* (2006.01)
*A61B 17/34* (2006.01)
*A61B 34/20* (2016.01)

(52) U.S. Cl.
CPC .............. *A61B 2017/00022* (2013.01); *A61B 2017/00106* (2013.01); *A61B 2017/003* (2013.01); *A61B 2017/00309* (2013.01); *A61B 2017/22094* (2013.01); *A61B 2017/3413* (2013.01); *A61B 2034/2063* (2016.02)

(56) References Cited

U.S. PATENT DOCUMENTS

| | | |
|---|---|---|
| 6,010,449 A | 1/2000 | Selmon et al. |
| 6,394,956 B1 | 5/2002 | Chandrasekaran et al. |
| 6,416,523 B1 | 7/2002 | Lafontaine |
| 7,785,261 B2 | 8/2010 | Maschke |
| 7,854,740 B2 | 12/2010 | Carney |
| 8,007,440 B2 | 8/2011 | Magnin et al. |
| 8,374,680 B2 | 2/2013 | Thompson |
| 8,668,709 B2 | 3/2014 | Nita et al. |
| 8,702,609 B2 | 4/2014 | Hadjicostis |
| 8,852,166 B1 | 10/2014 | Keilman et al. |
| 8,936,553 B2 | 1/2015 | Stigall et al. |
| 8,956,375 B2 | 2/2015 | Nita et al. |
| 9,162,046 B2 | 10/2015 | Hill et al. |
| 9,283,034 B2 | 3/2016 | Katoh et al. |
| 9,387,006 B2 | 7/2016 | Shturman |
| 9,402,646 B2 | 8/2016 | Nita |
| 9,474,506 B2 | 10/2016 | Magnin et al. |
| 9,545,263 B2 | 1/2017 | Lenihan et al. |
| 9,561,023 B2 | 2/2017 | Raabe et al. |
| 9,713,730 B2 | 7/2017 | Mathur et al. |
| 9,949,754 B2 | 4/2018 | Newhauser et al. |
| 9,986,917 B2 | 6/2018 | Haverkost et al. |
| 2005/0113688 A1 | 5/2005 | Nita et al. |
| 2005/0216044 A1 | 9/2005 | Hong |
| 2007/0066888 A1 | 3/2007 | Maschke |
| 2008/0294037 A1 | 11/2008 | Richter |
| 2008/0312673 A1 | 12/2008 | Viswanathan et al. |
| 2009/0131798 A1 | 5/2009 | Minar et al. |
| 2009/0264771 A1 | 10/2009 | Houben et al. |
| 2009/0292204 A1 | 11/2009 | Pansky |
| 2012/0059241 A1 | 3/2012 | Hastings et al. |
| 2012/0283565 A1 | 11/2012 | Richter |
| 2014/0180069 A1 | 6/2014 | Millett |
| 2016/0051323 A1* | 2/2016 | Stigall .................. A61B 17/22 600/407 |
| 2017/0156691 A1 | 6/2017 | Cabrera-Munoz et al. |
| 2020/0029948 A1 | 1/2020 | Wong et al. |

\* cited by examiner

STEERABLE CROSSING CATHETER

CROSS REFERENCE TO RELATED APPLICATIONS

This application claims the benefit of and priority to U.S. Provisional Patent Application Ser. No. 62/969,252 filed on Feb. 3, 2020, the disclosure of which is incorporated herein by reference.

TECHNICAL FIELD

The present disclosure pertains to medical devices, and methods for manufacturing medical devices. More particularly, the present disclosure pertains to medical devices for crossing vascular occlusions.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A steerable crossing catheter system is disclosed. The steerable crossing catheter system comprises: an elongate catheter shaft having a proximal end region, a steerable distal end region, and a lumen extending therethrough; a core disposed within the lumen, the core having a distal end; a penetrating member coupled to the distal end; and a sensing assembly disposed adjacent to the distal end, the sensing assembly being configured to estimate the location of the core within a body lumen.

Alternatively or additionally to any of the embodiments above, the steerable distal end region includes a steering member.

Alternatively or additionally to any of the embodiments above, the steering member includes a tubular member having a plurality of slots formed therein.

Alternatively or additionally to any of the embodiments above, further comprising an actuator coupled to the steering member.

Alternatively or additionally to any of the embodiments above, the core is slidably disposed within the lumen.

Alternatively or additionally to any of the embodiments above, the sensing assembly includes an ultrasound transducer.

Alternatively or additionally to any of the embodiments above, the penetrating member includes a pointed tip at the distal end of the core.

Alternatively or additionally to any of the embodiments above, the penetrating member includes an angled region at the distal end of the core.

A method for crossing a venous occlusion is disclosed. The method comprises: advancing a medical device system through a vein to a position adjacent to a venous occlusion; wherein the medical device system includes a steering member, a penetrating tip, and a sensing assembly; advancing the penetrating tip into engagement with the venous occlusion; estimating the position of the medical device system within the vein using the sensing assembly; and steering the medical device system with the steering member.

Alternatively or additionally to any of the embodiments above, the medical device system includes a catheter and a core disposed within the catheter.

Alternatively or additionally to any of the embodiments above, the steering member is disposed along a distal end region of the catheter.

Alternatively or additionally to any of the embodiments above, the penetrating tip is disposed adjacent to a distal end of the core.

Alternatively or additionally to any of the embodiments above, the sensing assembly is disposed adjacent to a distal end of the core.

Alternatively or additionally to any of the embodiments above, the sensing assembly includes an ultrasound transducer.

Alternatively or additionally to any of the embodiments above, estimating the position of the medical device system within the vein using the sensing assembly includes emitting ultrasonic energy with the ultrasound transducer.

Alternatively or additionally to any of the embodiments above, steering the medical device system with the steering member includes steering the medical device system so that the penetrating tip avoids contact with the vein.

A medical device system is disclosed. The medical device system comprises: a catheter; a steering member coupled to the catheter; a core disposed within the catheter; a penetrating member coupled to the core; and a sensing assembly coupled to the core, the sensing assembly being configured to estimate the location of the core within a body lumen during a medical intervention to cross a venous occlusion.

Alternatively or additionally to any of the embodiments above, the steering member includes a tubular member having a plurality of slots formed therein.

Alternatively or additionally to any of the embodiments above, further comprising an actuator coupled to the steering member.

Alternatively or additionally to any of the embodiments above, the sensing assembly includes an ultrasound transducer.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
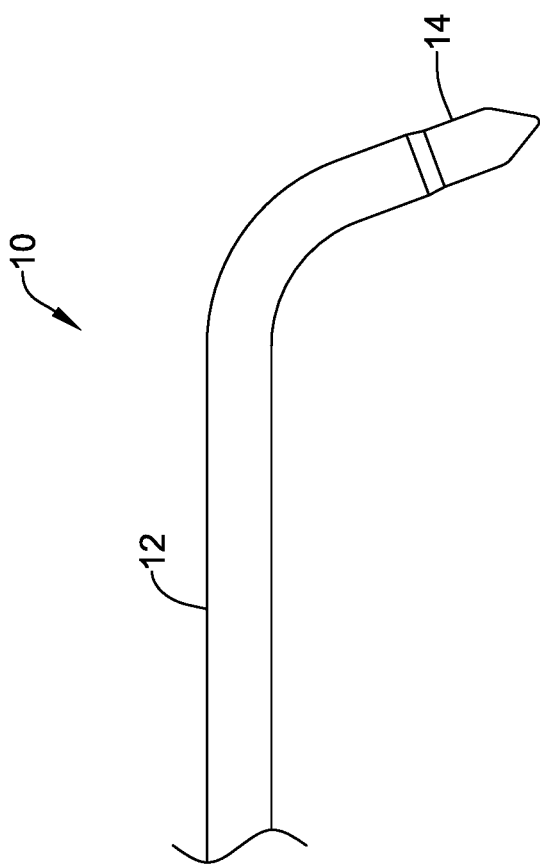
FIG. 1 is a side view of an example medical device assembly.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Vascular occlusions can result in serious health complications. For example, occlusions along the venous system can result in the pooling of blood in the lower extremities, leg swelling, skin changes, pain, ulcers, and/or the like. Treating venous occlusions generally includes the restoration of venous outflow back to the heart. Some example treatments may include angioplasty, stenting, and/or the like. In order to implement such treatments, it may be useful to pass a device such as a catheter and/or a guidewire through the occlusion. Unlike arterial occlusions that tend to become calcified, venous occlusions may have a tendency to become tough or hardened more like scar tissue. Because of this, the occlusion may tend to blend together with the vessel wall such that attempting to cross the occlusion with a medical device could bring the medical device into close proximity with the vessel wall. In some cases, attempts to cross the occlusion could result in damage to the vessel wall. Disclosed herein are medical device systems that can be used to cross an intravascular (e.g., venous) occlusion such a chronic total occlusion (e.g., a chronic total venous occlusion). Some of the features of these medical device systems are disclosed herein.

FIG. 1 schematically depicts an example medical device system 10. The medical device system 10 includes a shaft or catheter 12 and a core 14. In some instances, the core 14 is secured to and/or fixed to the catheter 12. In other instances, the core 14 is free from direct attachment to the catheter 12. For example, the core 14 may be slidably disposed within the lumen of the catheter 12. In such instances, the core 14 may be disposed within the catheter 12 during a crossing procedure. At a suitable time during a crossing procedure, the core 14 can be removed from the catheter 12. This may allow a guidewire to be passed through the catheter 12, another device such as a treatment device to be passed through the catheter 12, another "core" device to be passed through the catheter 12, etc.

Figure 2:
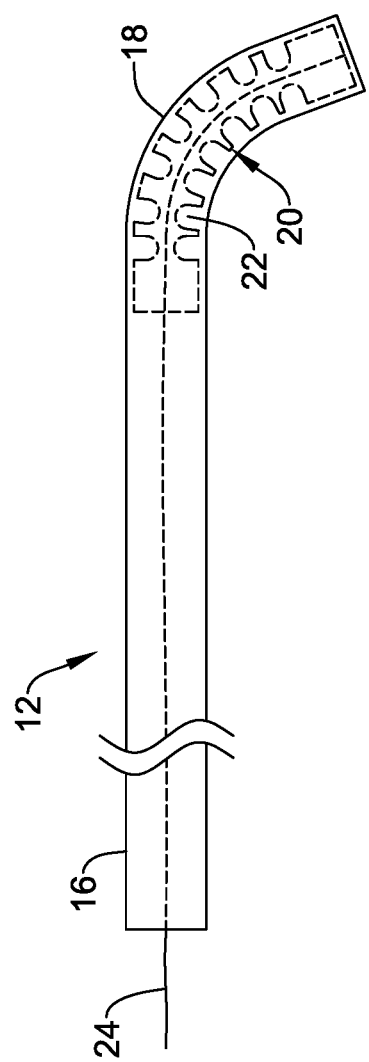
FIG. 2 is a side view of an example medical device.

FIG. 2 illustrates the catheter 12. In at least some instances, the catheter 12 may be similar in form and function to a guide catheter. The catheter 12 may include a proximal portion 16 and a distal portion 18. Structurally, the catheter 12 may include one or more layers of material. For example, the catheter 12 may include an inner layer or liner, which may be formed from a lubricious material. In some instances, a reinforcement layer may be disposed along the inner liner. The reinforcement layer may include a braid, coil, and/or the like. In some instances, an outer layer or sleeve may be disposed along the reinforcement layer. The outer layer may have a constant shore hardness or stiffness along its length or may include sections with differing levels of hardness/stiffness. This is just one example construction of the catheter 12. Other constructions are contemplated.

In some instances, the catheter 12 may include one or more features that allow the catheter 12, for example the distal portion 18 of the catheter 12, to be steerable. For example, the catheter 12 may include a steering member 20. In this example, the steering member 20 takes the form of a tube or tubular member having a plurality of slots 22 formed therein. The slots 22 may be disposed along one or more sides of the steering member 20 so that the steering member 20 may have one or more (e.g., one, two, three, four, or more) preferred bending directions. One or more actuators 24 may be coupled to the steering member 20. In this example, the actuator 24 may take the form of a pull wire coupled to the steering member 20 (e.g., adjacent to a distal end of the steering member 20) and extending proximally therefrom. The actuator 24 may allow a clinician to cause the catheter 12 to bend, curve, or otherwise change in shape. Thus, a clinician can use the actuator 24 to help navigate or steer the catheter 12 during an intravascular procedure. Some examples of suitable steering members and/or structures that may be incorporated into the catheter 12 in order to make the catheter 12 steerable include those disclosed in U.S. Pat. No. 9,162,046, the entire disclosure of which is herein incorporated by reference.

Figure 3:
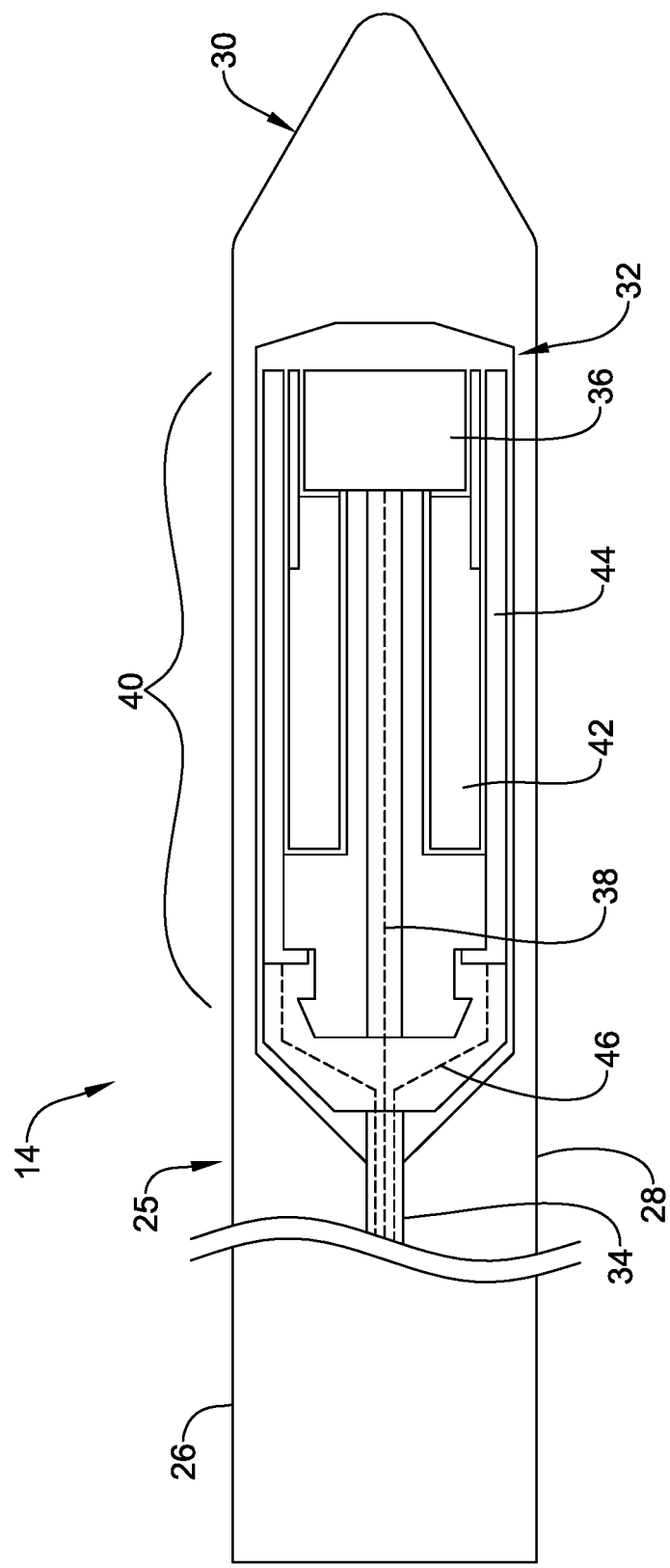
FIG. 3 is a side view of an example medical device.

FIG. 3 illustrates the core 14. The core 14 may take the form of a shaft 25 having a proximal end region 26 and a distal end region 28. In some instances, the core 14 may include a guidewire lumen (not shown) generally extending at least partially therethrough. The core 14 includes a number of structural features. For example, the core 14 may have a penetrating member or tip 30 coupled to the distal end region 28. The penetrating tip 30 may be generally configured to aid in engaging, penetrating, and ultimately crossing an intravascular occlusion. As such, the penetrating tip 30 may have a shape or configuration that could be described as being sharp or sharpened, pointed, and/or the like.

The core 14 may also include a sensing and/or imaging assembly 32. The form of the sensing and/or imaging assembly 32 may vary. For the purposes of this disclosure, the terms "sensing and/or imaging" may be understood to mean that structures typically used for sensing as well as structures typically used for imaging can make up parts of the sensing and/or imaging assembly 32 and such structures can be used to gather/collect information useful for aiding a clinician during a crossing procedure. For example, the sensing and/or imaging assembly 32 may take the form of an intravascular ultrasound (IVUS) assembly and/or at least one ultrasound transducer. An ultrasound transducer, for example, can be used to emit and measure ultrasonic reflections from within the vessel in order to estimate the tissue properties adjacent to the core 14 and, ultimately, use these properties to estimate the location of the core 14 within the vessel. For example, an occlusion and/or the tissue adjacent to the occlusion may include collagen. The type of collagen (e.g., type I vs. type III collagen) can vary through an occlusion (e.g., where the concentration of type III collagen tends to increase from the center of an occlusion toward the edge). Surrounding tissue and/or the vessel wall, conversely, may have a higher concentration of type I collagen. Because type I collagen and type III collagen reflect ultrasonic energy differently, a clinician can use the sensing and/or imaging assembly 32 to estimate the relative location of the core 14 within the vessel by sensing/imaging the different types of collagen adjacent to the core 14. More particularly, the sensing and/or imaging assembly 32 can be used to determine whether or not the core 14 is approaching tissue (e.g., the vessel wall) during a crossing procedure by sensing/imaging the type of collagen adjacent to the sensing and/or imaging assembly 32 within the vessel.

In some crossing procedures, a stent may already be in place adjacent to the occlusion. The sensing and/or imaging assembly 32 can also be used to sense/visualize the stent in order to help cross the occlusion. In such instances, the stent may provide another indicator of the location of the vessel wall that can be used to help reduce the likelihood of engaging/damaging the vessel wall.

In instances where the sensing and/or imaging assembly 32 includes an ultrasound transducer, the core 14 may include a number of structural features commonly used with ultrasound and/or IVUS devices. For example, the sensing and/or imaging assembly 32 may include a sensing/imaging device or transducer 36 that is coupled to a drive cable 34. For example, the sensing/imaging transducer 36 may include an ultrasound transducer or an array of (e.g., two or more) ultrasound transducers. One or more conductive member 38 may be coupled to the sensing/imaging transducer 36. The core 14 may also include a motor 40. The motor 40 may include a magnet 42 that can be driven to rotate by one or more magnetic field windings 44. One or more current lines 46 may be coupled to the windings 44. The motor 40 can be utilized to rotate the sensing and/or imaging assembly 32. These structures are just examples. Additional/different structures may be utilized. For example, in some instances, the sensing/imaging transducer 36 can be rotated by rotating the drive cable 34. In some of these and in other instances, the core 14 can be rotated in order to point the sensing/imaging transducer 36 in a variety of different directions.

In some instances, the sensing/imaging transducer 36 generally points to or is oriented in a direction substantially normal to the longitudinal axis of the core 14. In other words, the sensing/imaging transducer 36 may be pointed to the side or otherwise configured to sense/image objects alongside the core 14. In such instances, rotation of the sensing and/or imaging assembly 32 (and/or the sensing/imaging transducer 36), for example by the motor 40 or by rotating the drive cable 34, allows for sensing/imaging data to be gathered/collected from a plurality of different vantage points about the core 14. In other instances, the sensing/imaging transducer 36 may be pointed in the longitude direction. In some of these instances, the sensing/imaging transducer 36 may interact with other structures such as mirror and/or mirror holder (not shown). In such instances, the motor 40 may be used to rotate the mirror so that sensing/imaging data can be gathered/collected from a plurality of different vantage points about the core 14. Some examples of sensing and/or imaging assemblies and/or sensing/imaging transducers 36 that may utilized with the core 14 are disclosed in U.S. Patent Application Pub. No. US 2012/0059241, the entire disclosure of which is herein incorporated by reference.

While the sensing/imaging transducer 36 may take the form of or otherwise include an ultrasound transducer, this is not intended to be limiting. For example, the sensing and/or imaging assembly 32 may include different structural features including, but not limited to, an impedance sensor and/or electrode, an optical system/sensor, a biochemical system/sensor, a mechanical/piezo-electric sensor, combinations therefor, and/or the like. Such structures may be used similarly to the sensing and/or imaging assembly 32 in order to estimate the position of the core 14 within the vessel. For example, when using an impedance sensor (e.g., which may be disposed along the core 14, the catheter 12, or both) a venous occlusion may be more electrically resistive than surrounding tissue. Thus, an electrical pulse from an impedance electrode to a grounding pad disposed on the patient may provide an impedance/resistance value/profile that can be used to estimate the position of the core 14 within the vessel. When using an optical system, fluorescence spectroscopy can be used to characterize tissue. For example, different types of collagen may reflect light differently such that processing the reflected light (e.g., via a reflected wavelength pattern, a reflected light intensity, combinations thereof, etc.) may be used to estimate the position of the core 14 within the vessel. When using a biochemical sensor, a probe may be coated, for example, with lysyl oxidase, which may interact with lysine (e.g., which is a building block of collagen) and create an electrical signal that can be measured and translated into collagen concentration and, thus, estimate the position of the core 14 within the vessel. When using a mechanical/piezo-electric sensor, an electrical signal may be used in response to mechanical pressure changes during engagement with occlusions. Such sensing can be used estimate the position of the core 14 within the vessel.

While the above discussion is directed to a sensing and/or imaging assembly 32 that is a component of the core 14, other medical device systems are contemplated that either additionally or alternatively incorporate a sensing and/or imaging assembly into the catheter 12. For example, an ultrasound transducer can be disposed along the distal portion 18 of the catheter 12. Such an ultrasound transducer can be used analogously to the sensing and/or imaging assembly 32 described herein. Alternative sensing and/or imaging assemblies can be incorporated into the catheter 12.

Collectively, the structural features of the catheter 12 and the core 14 may allow the medical device system 10 to efficiently cross an intravascular occlusion (e.g., a venous occlusion). For example, the medical device system 10 includes the ability to engage and/or pierce into an occlusion (e.g., via the penetrating tip 30), estimate the position of the medical device system 10 within the vessel (e.g., via sensing and/or imaging assembly 32), and steer the medical device system 10 (e.g., via the steering member 20) so that contact with or damage to the vessel wall can be minimized/avoided during a crossing procedure.

Figure 4:
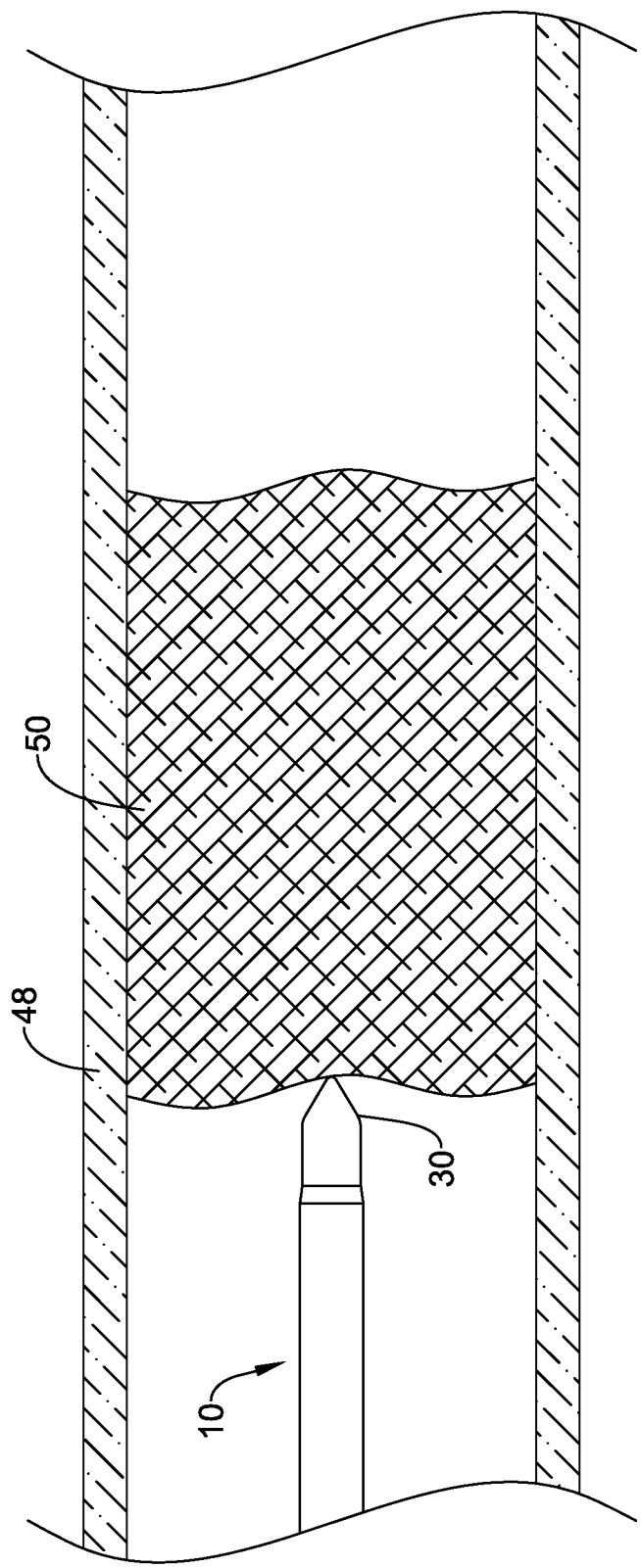
FIGS. 4-6 illustrate an example use of an example medical device assembly.
Figure 5:
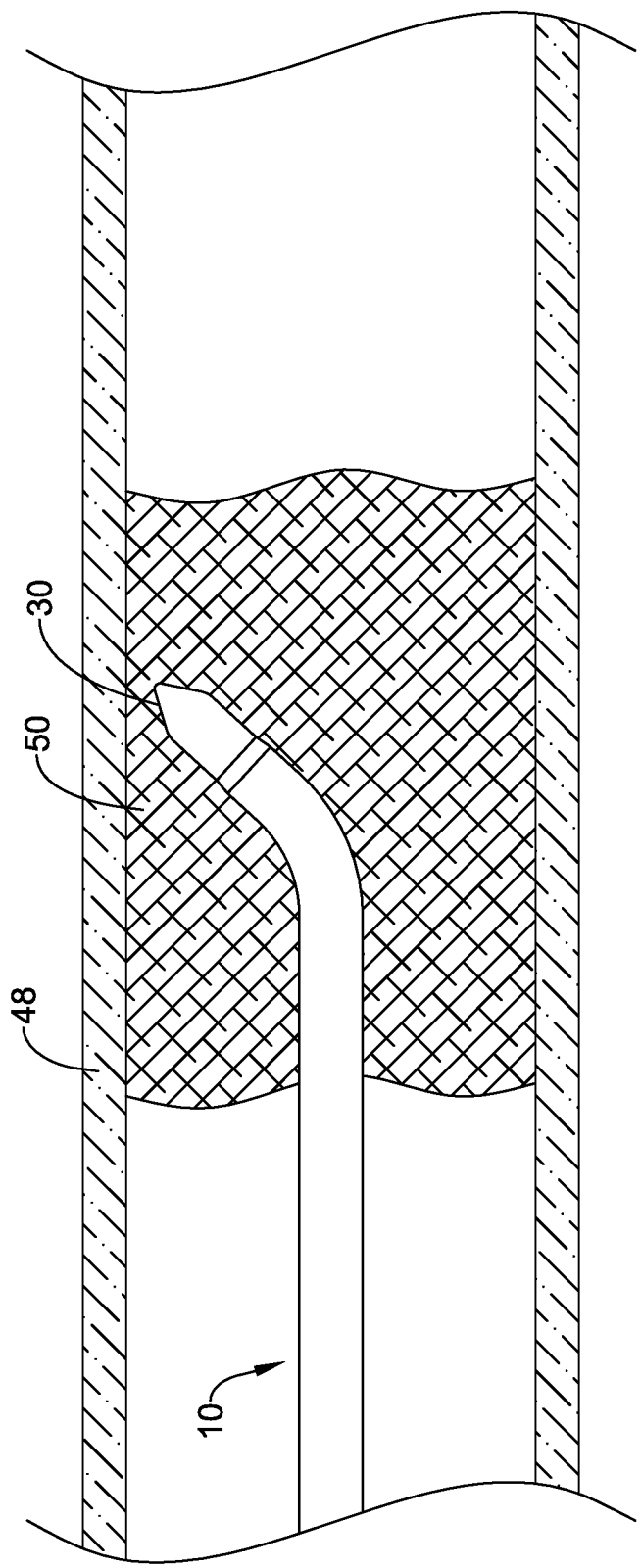
Figure 6:
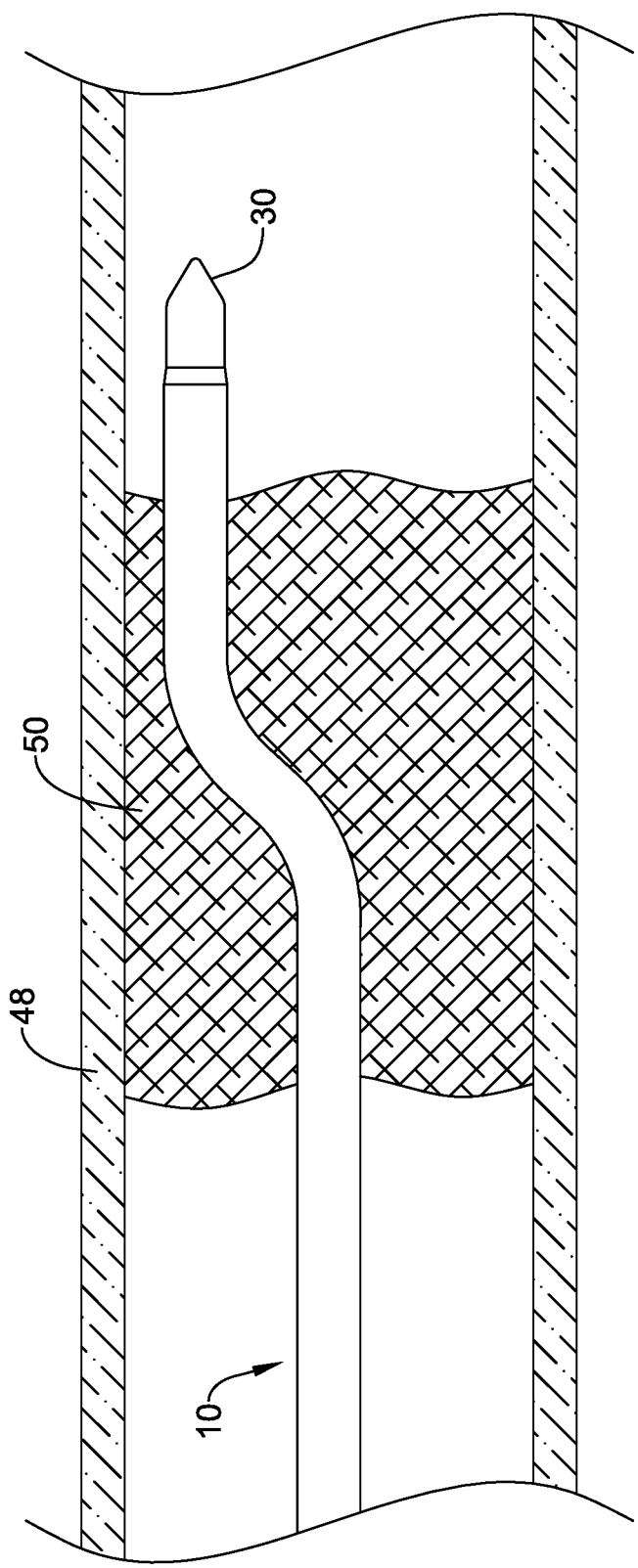

FIGS. 4-6 depict an example use of the medical device system 10 during a crossing procedure. Here it can be seen how the structural features of the catheter 12 and the core 14 desirably impact the crossing procedure. For example, the medical device system 10 may be navigated through a blood vessel 48 to a position adjacent to an occlusion 50. When doing so, the core 14 may be disposed within the catheter 12 such that the penetrating tip 30 extends distally from the distal portion 18 of the catheter 12 during navigation. Upon approaching the occlusion 50, the penetrating tip 30 may engage the occlusion 50 as shown in FIG. 4. When doing so, the penetrating tip 30 may begin to pierce through the occlusion 50 such that the medical device system 10 begins to cross the occlusion 50. While passing through the occlusion 50, the sensing and/or imaging assembly 32 can be utilized in order to estimate the position of the medical device system 10 within the vessel 48 and to monitor whether or not the medical device system 10 is approaching the wall of the vessel 48. At some point during the crossing procedure, it may be desirable to steer the catheter 12 in order to advance the medical device system 10 through the occlusion 50. For example, the penetrating tip 30 may encounter a region of the occlusion 50 that is not easily passed (e.g., the occlusion 50 is tough or hardened) or the penetrating tip 30 may begin to approach the wall of the vessel 48. When this happens, a clinician may utilize the steering member 20 to bend or steer the distal portion 18 of the catheter 12 away from the toughened region and/or away from the wall of the vessel 48. The steering of the medical device system 10 is schematically depicted in FIG. 5. The crossing procedure may include additional monitoring of the position of the medical device system 10 within the vessel 48 and/or one or more additional steering processes until the medical device system 10 is able to successfully cross the occlusion 50 as depicted in FIG. 6. In some instances, when the medical device system 10 has crossed the occlusion 50, the core 14 can be removed from the catheter 12. Once the core 14 is removed, a guidewire, treatment device, or another medical device can be passed through the catheter 12 in order to implement a suitable treatment for the occlusion 50.

Figure 11:
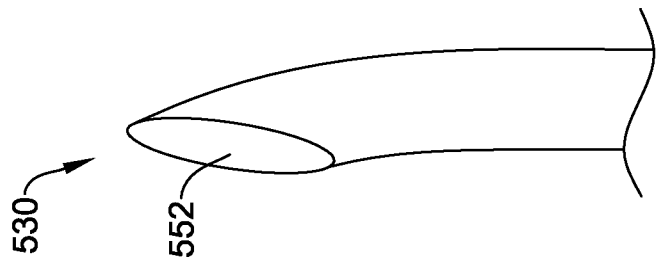
FIGS. 7-11 illustrate example penetrating tips.
Figure 10:
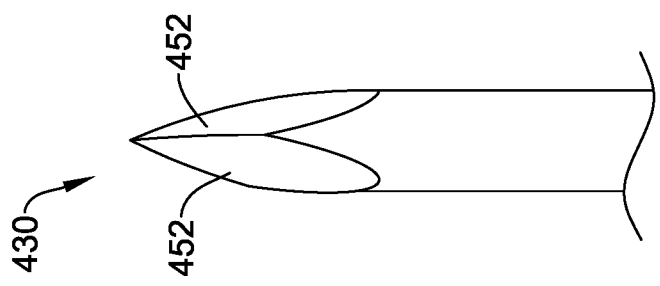
Figure 9:
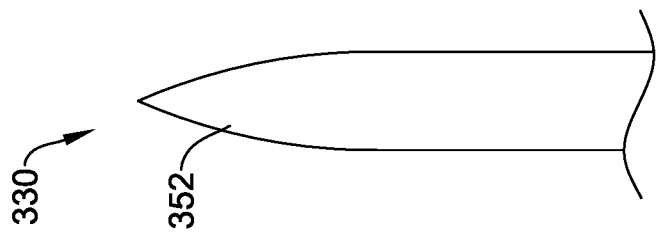
Figure 8:
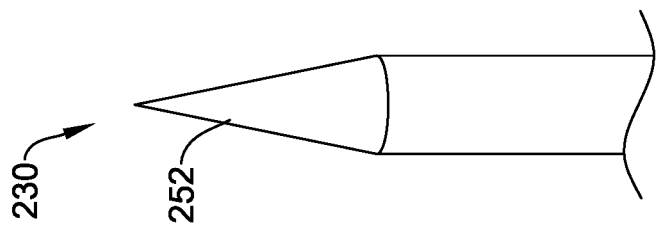
Figure 7:
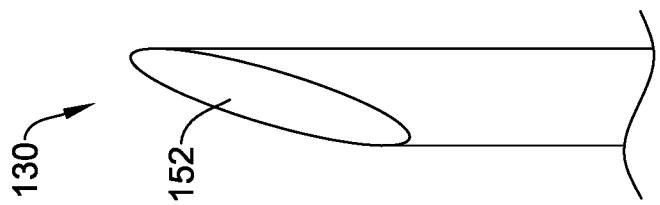

FIGS. 7-11 illustrate a number of alternative penetrating members/tips that may have similar form and function to the penetrating tip 30. As such, these alternative penetrating members can be incorporated into the medical device system 10. For example, FIG. 7 illustrates a penetrating tip 130 that includes an angled region 152. FIG. 8 illustrates a penetrating tip 230 with a conical region 252. FIG. 9 illustrates a penetrating tip 330 with a tapering region 352. FIG. 10 illustrates a penetrating tip 430 with a plurality of angled regions 452. FIG. 11 illustrates a penetrating tip 530 that is slightly curved and that includes an angled region 552. These penetrating tips are meant to be examples. Additional penetrating tips are contemplated.

Figure 12:
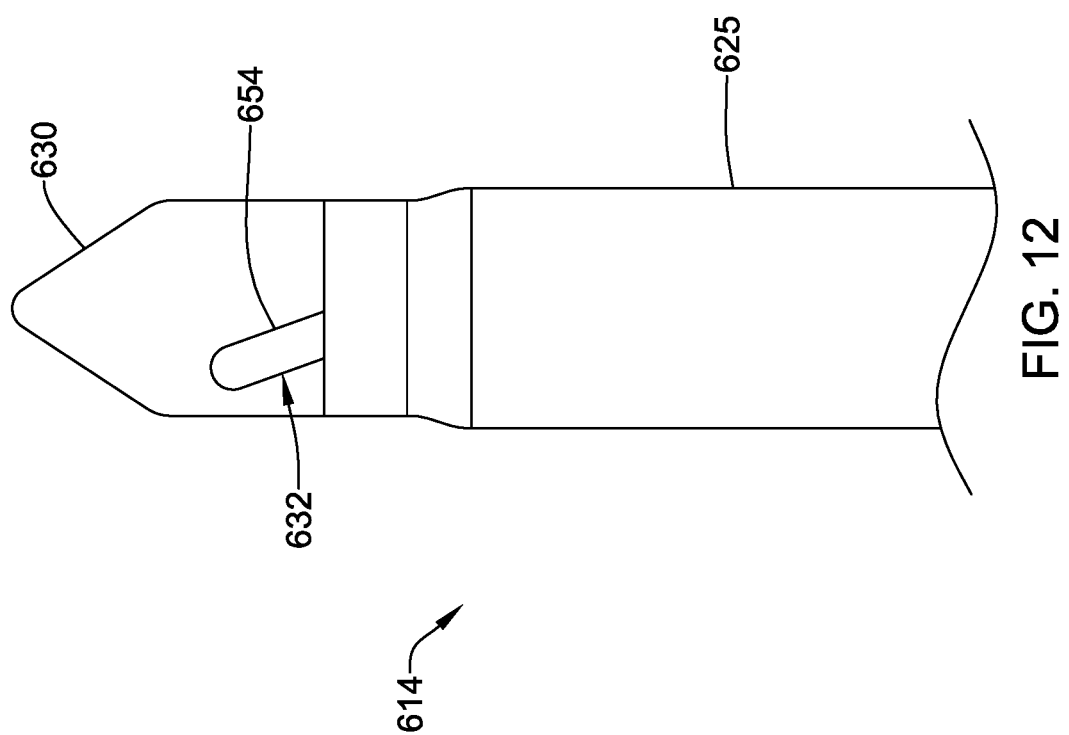
FIG. 12 is a side view of an example medical device.

FIG. 12 illustrates another example core 614 that may be similar in form and function to other cores disclosed herein. The core 614 may include a shaft 625 having a penetrating tip 630 coupled thereto. The core 614 may include a sensing and/or imaging assembly 632. The sensing and/or imaging assembly 632 may include an optical fiber 654. As discussed briefly herein, the optical fiber 654 may be used to shine light into the vessel. In order for the light to reach the tissue/occlusion, the penetrating tip 630 may be substantially transparent. Light that is reflected back can be used to characterize the tissue and/or estimate the position of the core 14 within the vessel. For example, different types of collagen may reflect light differently such that processing the reflected light (e.g., via a reflected wavelength pattern, a reflected light intensity, combinations thereof, etc. using fluorescence spectroscopy) may be used to estimate the position of the core 14 within the vessel.

Figure 13:
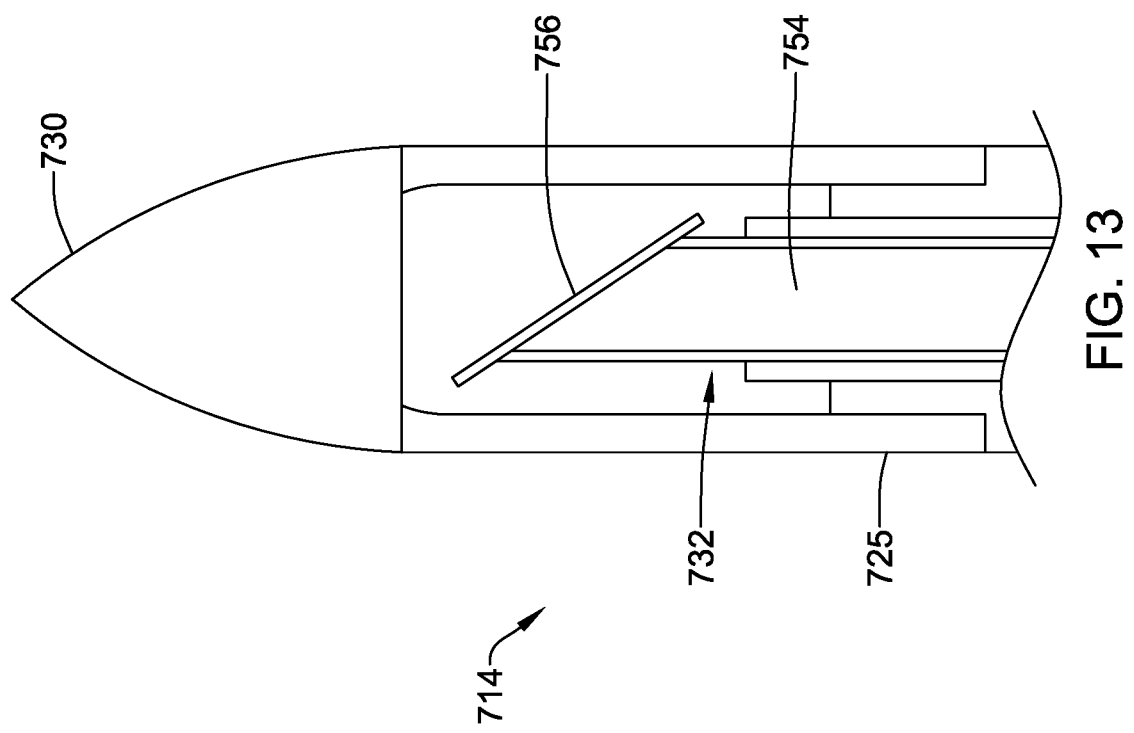
FIG. 13 is a side view of an example medical device.

FIG. 13 illustrates another example core 714 that may be similar in form and function to other cores disclosed herein. The core 714 may include a shaft 725 having a penetrating tip 730 coupled thereto. The core 714 may include a sensing and/or imaging assembly 732. The sensing and/or imaging assembly 732 may include an optical fiber 754 and a reflective member 756. In this example, a portion of shaft 725 may be substantially transparent so that light emitted from the optical fiber 754 can reach the tissue/occlusion. The reflective member 756 may help direct the light to transparent regions of the shaft 725.

The materials that can be used for the various components of the medical device system 10 may include those commonly associated with medical devices. For simplicity purposes, the following discussion makes reference to the catheter 12. However, this is not intended to limit the devices and methods described herein, as the discussion may be applied to other structures or devices disclosed herein.

The catheter 12 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device system 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device system 10 to achieve the same result.

In some embodiments, a degree of Magnetic Resonance Imaging (MRI) compatibility is imparted into the medical device system 10. For example, the medical device system 10, or portions thereof, may be made of a material that does not substantially distort the image and create substantial artifacts (e.g., gaps in the image). Certain ferromagnetic materials, for example, may not be suitable because they may create artifacts in an MRI image. The medical device system 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A steerable crossing catheter system, comprising:
   an elongate catheter shaft having a proximal end region, a steerable distal end region, and a lumen extending therethrough;
   a core disposed within the lumen, the core having a distal end;
   a penetrating member coupled to the distal end; and
   a sensing assembly coupled to the core adjacent to the distal end, wherein the sensing assembly includes an ultrasound transducer, the sensing assembly being configured to estimate the location of the core within a vessel by sensing different types of collagen adjacent to the sensing assembly within the vessel.

2. The steerable crossing catheter system of claim 1, wherein the steerable distal end region includes a steering member.

3. The steerable crossing catheter system of claim 2, wherein the steering member includes a tubular member having a plurality of slots formed therein.

4. The steerable crossing catheter system of claim 2, further comprising an actuator coupled to the steering member.

5. The steerable crossing catheter system of claim 1, wherein the core is slidably disposed within the lumen.

6. The steerable crossing catheter system of claim 1, wherein the penetrating member includes a pointed tip at the distal end of the core.

7. The steerable crossing catheter system of claim 1, wherein the penetrating member includes an angled region at the distal end of the core.

8. The steerable crossing catheter system of claim 1, wherein the core is fixed to the catheter.

9. The steerable crossing catheter system of claim 1, wherein the core is removable from the catheter.

10. A method for crossing a venous occlusion, the method comprising:
    advancing a medical device system through a blood vessel to a position adjacent to an occlusion;
    wherein the medical device system includes a steering member, a penetrating tip, a core, and a sensing assembly coupled to the core, wherein the sensing assembly includes an ultrasound transducer;
    advancing the penetrating tip into engagement with the occlusion;
    estimating the position of the medical device system within the blood vessel using the sensing assembly by emitting ultrasonic energy with the ultrasound transducer to sense different types of collagen adjacent to the sensing assembly within the blood vessel; and
    steering the medical device system with the steering member.

11. The method of claim 10, wherein the medical device system includes a catheter, and wherein the core is disposed within the catheter.

12. The method of claim 11, wherein the steering member is disposed along a distal end region of the catheter.

13. The method of claim 11, wherein the penetrating tip is disposed adjacent to a distal end of the core.

14. The method of claim 11, wherein the core is fixed to the catheter.

15. The method of claim 10, wherein steering the medical device system with the steering member includes steering the medical device system so that the penetrating tip avoids contact with the blood vessel.

16. A medical device system, comprising:
    a catheter;
    a steering member coupled to the catheter;
    a core disposed within the catheter;
    a penetrating member coupled to the core; and
    a sensing assembly coupled to the core, wherein the sensing assembly includes an ultrasound transducer, the sensing assembly being configured to estimate the location of the core within a blood vessel by sensing different types of collagen adjacent to the sensing assembly within the blood vessel during a medical intervention to cross a venous occlusion in the blood vessel.

17. The medical device system of claim 16, wherein the steering member includes a tubular member having a plurality of slots formed therein.

18. The medical device system of claim 17, further comprising an actuator coupled to the steering member.

19. The medical device system of claim 16, wherein the core is fixed to the catheter.

20. The medical device system of claim 16, wherein the core is removable from the catheter.

\* \* \* \* \*